(12) United States Patent
Shin et al.

(10) Patent No.: US 8,643,845 B2
(45) Date of Patent: Feb. 4, 2014

(54) INTERFEROMETRIC SURFACE INSPECTION USING A SLIT-SHAPED REFERENCE BEAM FROM INSPECTION SURFACE

(75) Inventors: Eui-Shin Shin, Yongin (KR); Myeng Woo Nam, Yongin (KR); Jin-Han Park, Yongin (KR); Jae-Seok Park, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 671 days.

(21) Appl. No.: 12/926,622

(22) Filed: Nov. 30, 2010

(65) Prior Publication Data

US 2011/0128550 A1 Jun. 2, 2011

(30) Foreign Application Priority Data

Dec. 1, 2009 (KR) .......................... 10-2009-0117891

(51) Int. Cl.
*G01N 21/00* (2006.01)
*G01B 11/02* (2006.01)

(52) U.S. Cl.
USPC ....................................... 356/496; 356/237.3

(58) Field of Classification Search
USPC .................. 356/511–514, 504, 516, 496, 492
See application file for complete search history.

(56) References Cited

U.S. PATENT DOCUMENTS

| | | | |
|---|---|---|---|
| 3,964,830 A * | 6/1976 | Ikeda et al. | 356/512 |
| 4,928,527 A | 5/1990 | Burger et al. | |
| 5,251,010 A * | 10/1993 | Maltby, Jr. | 356/613 |
| 2006/0098206 A1 * | 5/2006 | Kim et al. | 356/495 |
| 2008/0259319 A1 | 10/2008 | Mitome | |

FOREIGN PATENT DOCUMENTS

| | | |
|---|---|---|
| JP | 2008-014935 A | 1/2008 |
| KR | 1991-0004225 B1 | 6/1991 |
| KR | 10-2005-0102324 A | 10/2005 |
| KR | 10-2007-0001777 A | 1/2007 |
| KR | 10-2007-0115358 A | 12/2007 |
| KR | 10-2008-0094581 A | 10/2008 |
| KR | 10-0890647 B1 | 3/2009 |

* cited by examiner

*Primary Examiner* — Hwa Lee
(74) *Attorney, Agent, or Firm* — Lee & Morse, P.C.

(57) ABSTRACT

Provided are a surface inspection apparatus and method capable of detecting foreign materials on the surface of a substrate, and a slit coater having the surface inspection apparatus. In the surface inspection apparatus, a slit lighting unit irradiates slit-shaped light. An optical system splits the slit-shaped light into two beams traveling along two different paths, is incident upon a subject, and extracts an interference image caused by combination of the two beams reflected from the subject. An imaging device captures the interference image to output an image signal. An analysis unit acquires a luminance value of the image signal, analyzes the luminance value in real time, and determines whether or not foreign materials are present.

22 Claims, 4 Drawing Sheets

INTERFEROMETRIC SURFACE INSPECTION USING A SLIT-SHAPED REFERENCE BEAM FROM INSPECTION SURFACE

BACKGROUND

1. Field

Embodiments relate to a surface inspection apparatus and method, and a slit coater using the same. More particularly, embodiments relate to a surface inspection apparatus and method capable of detecting foreign materials on the surface of a substrate so as to stably coat a coating layer on the substrate, and a slit coater having the surface inspection apparatus.

2. Description of the Related Art

In general, thin films carrying out specific functions, for instance, an oxide thin film, a metal thin film, and a semiconductor thin film are coated on a substrate in the semiconductor manufacturing and imaging device manufacturing fields. Here, the coating layers are patterned through exposure and development as needed.

Methods of forming such a coating layer include spin coating, slit coating, and so on. In spin coating, a coating solution is dropped on a substrate and the substrate is rotated at high speed to form a coating layer. In slit coating, a slit coater having a slit-shaped nozzle that is longer than a width of a substrate moves along the substrate to coat a coating solution on the substrate. In particular, the slit coater perform moves a slit die or nozzle at high speed in close proximity to the substrate to be coated in order to secure process performance.

Since slit coating is performed without rotating the substrate, foreign materials may readily attach to the substrate. When the foreign materials are present on the substrate, process performance may be impaired and/or the slit die or nozzle may be damaged or misaligned when colliding with the foreign materials. For this reason, a device for detecting the foreign materials on the substrate is disposed in front of the nozzle in a direction in which the coating solution is supplied.

SUMMARY

It is therefore a feature of an embodiment to provide a surface inspection apparatus and method capable of detecting foreign materials on the surface of a subject.

It is therefore another feature of an embodiment to provide a surface inspection apparatus and method capable of effectively detecting small foreign materials in real time while moving at high speed.

It is yet another feature of an embodiment to provide a slit coater, which has the surface inspection apparatus and is able to prevent a slit nozzle from being damaged or broken by foreign materials located on a substrate.

At least one of the above and other features and advantages may be realized by providing a surface inspection apparatus including a slit lighting unit outputting slit-shaped light, an optical system configured to split the slit-shaped light into two beams traveling along two different paths, direct the two beams onto a subject, and extract an interference image by combining the two beams reflected from the subject, an imaging device configured to capture the interference image and to output an image signal in response thereto, and an analysis unit configured to acquire a luminance value of the image signal, analyze the luminance value in real time, and determine whether or not foreign materials are present.

The optical system may include a splitter splitting the slit-shaped light into a first beam traveling along a first path and a second beam traveling along a second path, a first objective lens in the first path, and a reflective mirror, a piezo-electric transducer (PZT) unit, and a second objective lens in the second path. The reflective mirror may be between the splitter and the PZT unit, the reflective mirror directing the second beam towards the subject along the second path. The PZT unit may be installed in front of the second objective lens and configured to displace the second objective lens in a vertical direction relative to the subject. The first and second objective lenses may be identical. The first and second paths may be configured to maximize constructive interference when no foreign materials are present. The splitter may combine the first and second beams reflected from the subject.

The imaging device may include a line scan camera.

At least one of the above and other features and advantages may be realized by providing a surface inspection method of inspecting presence of foreign materials on a subject, the method including splitting slit-shaped light irradiated from a slit lighting unit into a first beam traveling along a first path and a second beam traveling along a second path, directing the first and second beams onto the subject, combining the first and second beams reflected from the subject to cause interference, capturing an image due to the interference and outputting an image signal, and analyzing a luminance value of the image signal to determine whether or not foreign materials are present.

Providing the first beam onto the subject may be through a first objective lens disposed in the first path. Providing the second beam onto the subject may be through a reflective mirror, a piezo-electric transducer (PZT) unit, and a second objective lens disposed in the second path.

The first and second paths may be configured to maximize constructive interference when the reflected first and second beams are combined and no foreign material is present.

Analyzing may include determining that no foreign materials are present when the luminance value is high and that foreign materials are present when the luminance value is low.

At least one of the above and other features and advantages may be realized by providing a slit coater including a nozzle unit configured to apply a coating solution to a substrate and a surface inspection apparatus configured to inspect a presence of foreign materials on the substrate and installed in front of the nozzle unit in a direction in which the coating solution is applied.

BRIEF DESCRIPTION OF THE DRAWINGS

The above and other features and advantages will become more apparent to those of ordinary skill in the art by describing in detail exemplary embodiments with reference to the attached drawings, in which.

DETAILED DESCRIPTION

Figure 1:
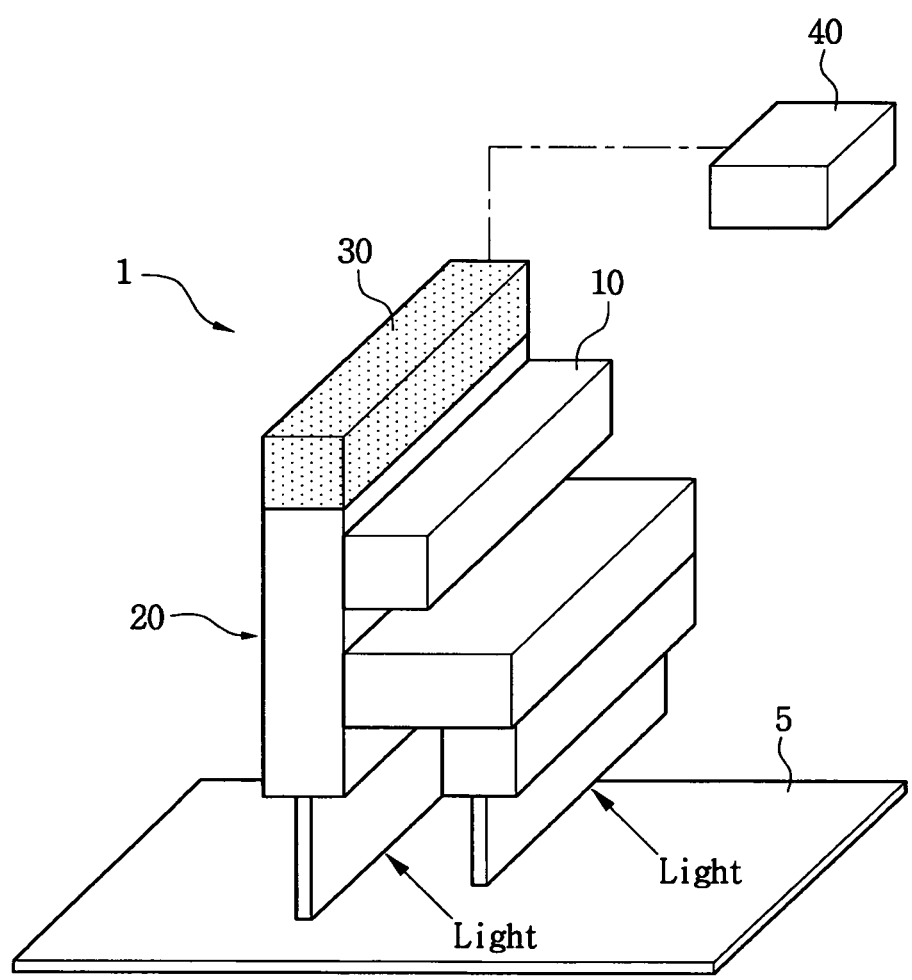
FIG. 1 illustrates a perspective view of a surface inspection apparatus according to an exemplary embodiment.

Korean Patent Application No. 10-2009-0117891, filed on Dec. 1, 2009, in the Korean Intellectual Property Office, and entitled: "Surface Inspection Apparatus and Method, and Slit Coater Using the Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

Figure 2:
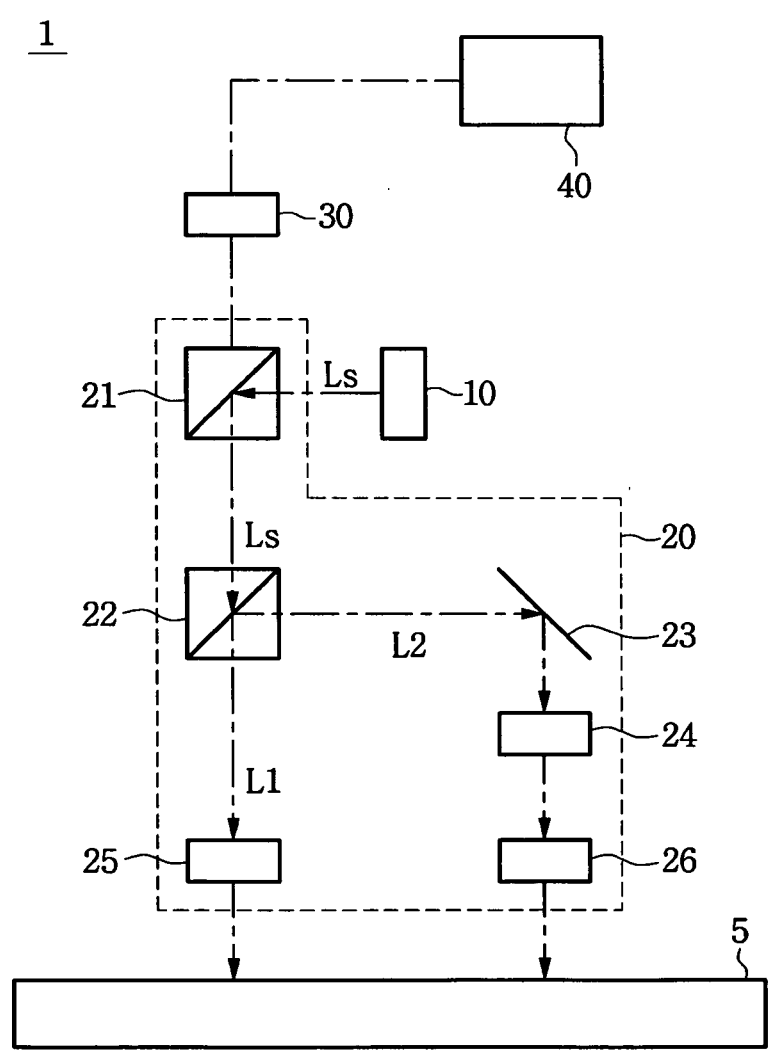
FIG. 2 illustrates a block diagram of a configuration of the surface inspection apparatus of FIG. 1 according to an exemplary embodiment.

FIG. 1 illustrates a perspective view of a surface inspection apparatus according to an exemplary embodiment. FIG. 2 illustrates a block diagram of a configuration of the surface inspection apparatus of FIG. 1 according to an exemplary embodiment.

Referring to FIGS. 1 and 2, the surface inspection apparatus 1 according to an exemplary embodiment may include a slit lighting unit 10, an optical system 20, an imaging device 30, and an analysis unit 40.

The slit lighting unit 10 outputs slit-shaped light, e.g., by passing light emitted from a light source through a slit filter. The slit lighting unit 10 may be configured in the form of a lighting-only optical system capable of providing slit light. For example, a tungsten-halogen lamp, which is relatively inexpensive and has a long life, may be used as the light source.

The optical system 20 is configured to extract an interference image of a subject 5 using the slit-shaped light from the slit lighting unit 10. The optical system 20 is configured to provide the slit-shaped light to the subject 5 though two different paths to generate the interference image.

Referring to FIG. 2, the optical system 20 may include a first splitter 21, a second splitter 22, a reflective mirror 23, a piezo-electric transducer (PZT) unit 24, a first objective lens 25, and a second objective lens 26. The first and second objective lenses 25 and 26 may be identical.

The first splitter 21 switches the path of the slit-shaped light Ls from the slit lighting unit 10, i.e., directs the slit-shaped light Ls towards the subject 5. The second splitter 22 splits the slit-shaped light Ls incident from the first splitter 21 into a first beam L1 travelling along a first path and a second beam L2 travelling along a second path. Thus, after passing through the second splitter 22, the slit-shaped light Ls is split into the first beam L1 travelling along the first path and the second beam L2 travelling along the second path.

The first beam L1 is incident upon the subject 5 through the first objective lens 25. The second beam L2 is incident upon the subject 5 through the reflective mirror 23, the PZT unit 24, and the second objective lens 26. The first beam L1 and the second beam L2 are incident upon the subject 5 in a direction perpendicular to the subject 5.

Thus, the first objective lens 25 is disposed on the first path, and the reflective mirror 23, the PZT unit 24, and the second objective lens 26 are disposed on the second path. The reflective mirror 23 switches a travelling direction of the second beam L2 such that the second beam L2, which is split and incident by the second splitter 22, travels along the second path, i.e., directs the second beam L2 towards the subject 5. The PZT unit 24 may be in front of the second objective lens 26. The PZT unit 24 may be adjusted, e.g., in units of nanometers, to change its length depending on a voltage applied from the outside to thereby displace the second objective lens 26 in a direction along the light path.

The first and second paths have a path difference depending on a wavelength $\lambda$ of the light of the light source. After the first and second beams have been reflected from the subject 5, travel back along the first and second paths, respectively, and are combined at the second splitter 22, the path difference between the first and second light beams results in interference.

The first and second objective lenses 25 and 26 may be aligned relative to one another to maximize constructive interference when no foreign materials are present. This alignment may be realized by displacing the second objective lens 26 using the PZT unit 24.

The imaging device 30 collects the first and second beams L1 and L2 reflected and returning from the subject 5 through the first and second paths, and the first and second splitter 21, 22. The imaging device 30 thus captures an interference image of the subject 5 and outputs an image signal to the analysis unit 40.

The first and second beams L1 and L2 reflected from the subject 5 interfere due to a phase difference depending on a change in height of the subject 5 between where the first and second beams L1 and L2 are incident on the subject 5. Thus, presence of foreign materials may be assessed in accordance with changes to an interference pattern generated by the first and second beams L1 and L2. The image of the interference pattern is captured by the imaging device 30.

The interference pattern shows a phase difference of the subject 5 in the form of a contrast. When a phase difference is not present, e.g., when no foreign materials are present, the first and second beams constructively interfere, so an image signal output from the imaging device 30 has a high luminance value. When a phase difference is present, e.g., foreign materials are present, the first and second beams destructively interference, so that an image signal output from the imaging device 30 has a low luminance value. A line scan camera may be used as the imaging device 30.

The analysis unit 40 acquires the luminance value of the image signal output from the imaging device 30, analyzes it in real time, and determines whether or not the foreign materials are present.

Briefly referring to operation of the surface inspection apparatus shown in FIG. 1, slit-shaped light Ls from the slit lighting unit 10 is split into the first beam L1 and the second beam L2 using the second splitter 22. The first and second beams L1 and L2 are incident upon the subject 5 along first and second paths.

The first and second objective lenses 25 and 26 may be aligned so as to maximize constructive interference when no foreign materials are present. This alignment can be performed by adjusting the PZT unit 24 located in front of the second objective lens 26.

As noted above, the first beam L1 is incident upon the subject 5 through the first objective lens 25, and the second beam L2 is incident upon the subject 5 through the reflective mirror 23, the PZT unit 24, and the second objective lens 26.

The first and second beams L1 and L2 incident upon the subject 5 are reflected by the subject 5 to travel along the first and second paths again, and are combined at the second splitter 22 where they interfere. An image caused by the interference is captured by the imaging device 30. The analysis unit 40 analyzes a luminance value of the captured image and determines whether or not foreign materials are present.

Here, since the first and second objective lenses 25 and 26 are aligned to maximize constructive interference, the first and second paths are configured to maximize constructive interference when the reflected first and second beams are combined at the second splitter 22 and no foreign materials are present.

When there is no path difference between the reflected first and second beams L1 and L2, i.e., when no foreign material is present on the subject 5, the first and second beams L1 and L2 constructively interfere, resulting in a high luminance value. In contrast, when a there is a path difference between the reflected first and second beams L1 and L2, i.e., when foreign material is present on the subject 5 in one of the first and second paths, the first and second beams L1 and L2 destructively interfere due to this path difference, resulting in a low luminance value.

The analysis unit 40 analyzes the variation of luminance value, and can determine whether or not the foreign materials are present. In detail, when the luminance value is high, the analysis unit 40 determines that no foreign materials are present. When the luminance value is low, the analysis unit 40 determines that the foreign materials are present.

Figure 3:
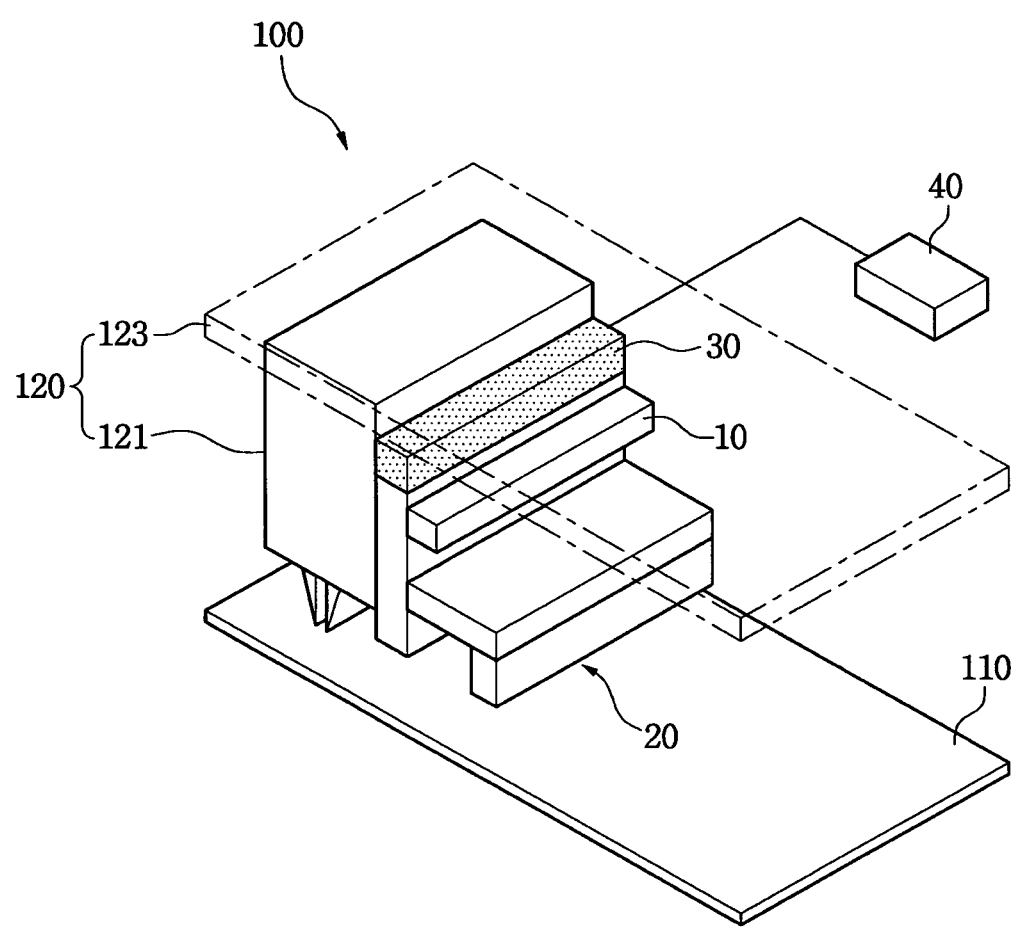
FIG. 3 illustrates a perspective view of an example of a slit coater having a surface inspection apparatus according to an exemplary embodiment.
Figure 4:
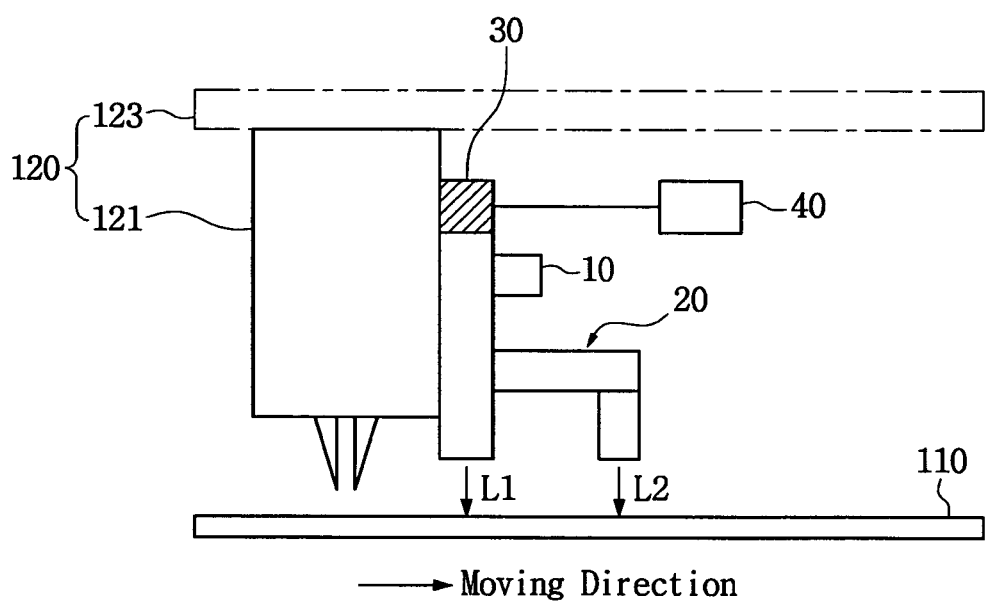
FIG. 4 illustrates a cross-sectional view of the slit coater of FIG. 3.

FIG. 3 illustrates a perspective view of an example of a slit coater having a surface inspection apparatus according to an exemplary embodiment. FIG. 4 illustrates a cross-sectional view of the slit coater of FIG. 3.

Referring to FIGS. 3 and 4, the slit coater 100 may include a nozzle unit 120 applying a coating solution to a substrate 110 and the surface inspection apparatus 1 for inspecting foreign materials on a surface of the substrate 110. The surface inspection apparatus 1 is illustrated in FIGS. 1 and 2, so a detailed description thereof will not be repeated.

The nozzle unit 120 may include a slit nozzle 121 discharging the coating solution to the substrate 110 and a nozzle support 123 supporting the slit nozzle 121. The slit nozzle 121 is separated from the surface of the substrate 110 and may discharge the coating solution to the substrate 110 while moving relative to the surface of the substrate 110.

The surface inspection apparatus 1 is installed in front of the nozzle unit 120 in a direction where the coating solution is applied. Thus, the surface inspection apparatus 1 may determine presence of the foreign materials on the substrate 110 before the nozzle unit 120 reaches that portion of the substrate 110. A method of inspecting the foreign materials has been described in detail with reference to FIGS. 1 and 2, and thus will be only briefly described below.

The slit-shaped light irradiated from the slit lighting unit 10 is split into the first beam L1 travelling along the first path and the second beam L2 travelling along the second path through the optical system 20. The first and second beams L1 and L2 are incident upon the substrate 110 offset from one another along the moving direction of the nozzle unit 120. The first and second paths may be configured to maximize constructive interference between the reflected first and second beams L1 and L2 at the second splitter 22.

The first and second beams L1 and L2 incident upon the substrate 110 are reflected to travel along the first and second paths again, and are combined at the second splitter 22 to interfere. An image caused by the interference is captured by the imaging device 30. The analysis unit 40 analyzes a luminance value of the captured image, thereby determining whether or not the foreign materials are present.

When the analysis unit 40 determines foreign material is present, remedial action may be taken. For example, that portion of the substrate 110 may be flagged for further inspection, the nozzle unit 120 may be stopped, the nozzle unit 120 may be raised to avoid the foreign material, and so forth.

In contrast with other detecting methods, use of interference imaging in accordance with embodiments may allow high speed detection of foreign material of a small size. For example, other methods may simply use a photo sensor to detect foreign material. However, when an interval between a sending section and a receiving section of the photo sensor increases, detecting performance may be reduced, making detection possible only when the foreign materials have a size of several millimeters or more. As another example, foreign material may be detected from light scattered on a surface of the foreign material when being incident upon the surface of the foreign material at an inclined angle. Although this may allow relatively high precision detection, however, a lighting section and a detecting section must be separated from each other at a predetermined angle. Further, precise arrangement between a subject to be measured and an optical system must always be maintained to measure scattered light, so detection while the optical system moves at high speed is difficult.

In contrast, use of interference imaging in accordance with embodiments may allow high speed detection of foreign material of a small size. Such detection may be performed in real time, allowing improper processing and/or damage to the nozzle unit to be reduced or avoided.

Exemplary embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A surface inspection apparatus, comprising:
a slit lighting unit outputting slit-shaped light;
an optical system configured to split the slit-shaped light into two beams traveling along two different paths, direct the two beams onto a subject, and extract an interference image by combining the two beams reflected from the subject;
an imaging device configured to capture the interference image and to output an image signal in response thereto; and
an analysis unit configured to acquire a luminance value of the image signal, analyze the luminance value in real time, and determine whether or not foreign materials are present.

2. The surface inspection apparatus as claimed in claim 1, wherein the optical system includes:
a splitter splitting the slit-shaped light into a first beam traveling along a first path and a second beam traveling along a second path;
a first objective lens in the first path; and
a reflective mirror, a piezo-electric transducer (PZT) unit, and a second objective lens in the second path.

3. The surface inspection apparatus as claimed in claim 2, wherein the reflective mirror is between the splitter and the PZT unit, the reflective mirror directing the second beam towards the subject along the second path.

4. The surface inspection apparatus as claimed in claim 2, wherein the PZT unit is configured to displace the second objective lens in a vertical direction relative to the subject.

5. The surface inspection apparatus as claimed in claim 4, wherein the PZT unit is configured to align the second objective lens relative to the first objective lens to maximize constructive interference when no foreign materials are present.

6. The surface inspection apparatus as claimed in claim 2, wherein the first and second objective lenses are identical.

7. The surface inspection apparatus as claimed in claim 2, wherein the splitter combines the first and second beams reflected from the subject.

8. The surface inspection apparatus as claimed in claim 1, wherein the imaging device includes a line scan camera.

9. A surface inspection method of inspecting presence of foreign materials on a subject, the method comprising:

splitting slit-shaped light irradiated from a slit lighting unit into a first beam traveling along a first path and a second beam traveling along a second path;

directing the first and second beams onto the subject, combining the first and second beams reflected from the subject to cause interference;

capturing an image due to the interference and outputting an image signal; and analyzing a luminance value of the image signal to determine whether or not foreign materials are present.

10. The surface inspection method as claimed in claim 9, wherein providing the first beam onto the subject is through a first objective lens disposed in the first path and providing the second beam onto the subject is through a reflective mirror, a piezo-electric transducer (PZT) unit, and a second objective lens disposed in the second path.

11. The surface inspection method as claimed in claim 9, wherein the first and second paths are configured to maximize constructive interference when the reflected first and second beams are combined and no foreign material is present.

12. The surface inspection method as claimed in claim 9, wherein analyzing includes determining that no foreign materials are present when the luminance value is high and that foreign materials are present when the luminance value is low.

13. A slit coater, comprising:

a nozzle unit configured to apply a coating solution to a substrate; and a surface inspection apparatus configured to inspect for a presence of foreign materials on the substrate and installed in front of the nozzle unit in a direction in which the coating solution is applied, the surface inspection apparatus including:

a slit lighting unit outputting slit-shaped light;

an optical system configured to split the slit-shaped light into two beams traveling along two different paths, direct the two beams onto a subject, and extract an interference image by combining the two beams reflected from the subject;

an imaging device configured to capture the interference image and to output an image signal in response thereto; and an analysis unit configured to acquire a luminance value of the image signal, analyze the luminance value in real time, and determine whether or not foreign materials are present.

14. The slit coater as claimed in claim 13, wherein the nozzle unit includes:

a slit unit configured to discharge the coating solution to the substrate; and a nozzle support supporting the slit nozzle.

15. The slit coater as claimed in claim 13, wherein the optical system includes:

a splitter splitting the slit-shaped light into a first beam traveling along a first path and a second beam traveling along a second path;

a first objective lens in the first path; and a reflective mirror, a piezo-electric transducer (PZT) unit, and a second objective lens in the second path.

16. The slit coater as claimed in claim 15, wherein the reflective mirror is between the splitter and the PZT unit, the reflective mirror directing the second beam towards the subject along the second path.

17. The slit coater as claimed in claim 15, wherein the PZT unit is configured to displace the second objective lens in a vertical direction relative to the subject.

18. The slit coater as claimed in claim 17, wherein the PZT unit is configured to align the second objective lens relative to the first objective lens to maximize constructive interference when no foreign materials are present.

19. The slit coater as claimed in claim 15, wherein the first and second objective lenses are identical.

20. The slit coater as claimed in claim 15, wherein the first and second paths are configured to maximize constructive interference when no foreign materials are present.

21. The slit coater as claimed in claim 15, wherein the splitter combines the first and second beams reflected from the subject.

22. The slit coater as claimed in claim 13, wherein the imaging device includes a line scan camera.

* * * * *